United States Patent [19]

Suzukamo et al.

[11] Patent Number: 4,720,601

[45] Date of Patent: Jan. 19, 1988

[54] PROCESS FOR PREPARING 5-ETHYLIDENE-2-NORBORNENE

[75] Inventors: Gohfu Suzukamo, Osaka; Masami Fukao, Shiga, both of Japan

[73] Assignee: Sumitomo Chemical Company Limited, Osaka, Japan

[21] Appl. No.: 896,959

[22] Filed: Aug. 15, 1986

[30] Foreign Application Priority Data

Oct. 21, 1985 [JP] Japan .............................. 60-235992
Nov. 21, 1985 [JP] Japan .............................. 60-262283

[51] Int. Cl.$^4$ .............................................. C07C 5/25
[52] U.S. Cl. ..................................... 585/377; 585/363
[58] Field of Search ................................ 585/377, 363

[56] References Cited

U.S. PATENT DOCUMENTS 3,897,509 7/1975 Nagase et al. ....................... 585/363

FOREIGN PATENT DOCUMENTS 769324 7/1970 Belgium .............................. 585/377

Primary Examiner—Asok Pal
Attorney, Agent, or Firm—Birch, Stewart, Kolasch & Birch

[57] ABSTRACT

5-Ethylidene-2-norbornene is effectively prepared by isomerization 5-vinyl-2-norbornene in the presence of at least one catalyst selected from a group consisting of a solid base catalyst which is prepared by reacting alumina and an alkali metal hydroxide at a temperature of 200° to 500° C. and then reacting the reaction produce with an alkali metal at a temperature of 180° to 350° C. and a solid base catalyst which is prepared by reacting water-containing alumina and an alkali metal in such an amount that corresponds to a molar equivalent of water contained in alumina at a temperature in a range between a melting point of the alkali metal and 500° C. and then reacting the reaction product with an alkali metal at a temperature of 180° to 350° C.

16 Claims, No Drawings

PROCESS FOR PREPARING 5-ETHYLIDENE-2-NORBORNENE

BACKGROUND OF THE INVENTION

1. Field of the Invention

The present invention relates to a process for preparing 5-ethylidene-2-norbornene (hereinafter referred to as "ENB"). Particularly, it relates to a process for preparing ENB by isomerizing 5-vinyl-2-norbornene (hereinafter referred to as "VNB") in the presence of a specific solid base catalyst.

2. Description of the Prior Art

ENB is the most promising compound as a third monomer of a terpolymer of ethylene, propylene and dienemonomer (EPDM rubber) and prepared by isomerizing VNB in the presence of a catalyst. VNB is produced by reacting 1,3-butadiene and cyclopentadiene.

As the isomerization catalysts, there are known liquid bases such as mixtures of an alkali metal hydroxide and an aprotic organic solvent, of an alkali metal amide and an amine, and of an organic alkali metal compound and an aliphatic amine. Such liquid bases, however, do not have enough catalytic activity so that a large amount of the expensive catalyst should be used. Further, since separation and recovering of the catalyst component from the reaction mixture are very difficult, the process requires complicated separation and recovering steps and consumes a large amount of energy.

There are also known solid isomerizatiion catalysts, for example, an alkali metal carried on an anhydrous carrier with a large surface area (e.g., activated carbon, silica gel, alumina and the like) (cf. J. Am. Chem. Soc., 82, 387 (1960)). The solid catalyst, however, has unsartisfactory handleability and less safety since it is ignited and loses activity on contact with air. This is because the alkali metal is only finely dispersed on the carrier. Further, the solid catalyst has insufficient isomerization performance.

The inventors have proposed a solid base catalyst for isomerizing olefins such as VNB, which do not suffer from the drawbacks of the conventional isomerization catalysts. The proposed catalyst is prepared from alumina, an alkali metal hydroxide and an alkali metal, or from water-containing alumina and an alkali metal. The solid base catalyst has higher stability to air and excellent isomerization activity of olefins such as VNB than the alkali metal dispersion catalyst (cf. Japanese patent publication Nos. 3274/1975 and 21378/1982).

SUMMARY OF THE INVENTION

One object of the present invention is to provide an improved catalyst for use in preparing ENB by isomerization of VNB.

Another object of the present invention is to provide a process for preparing ENB by isomerizing VNB in the presence of a solid base catalyst which has higher catalytic activity and exerts its catalytic effect in a smaller quantities than the aforementioned catalysts.

These and other objects are accomplished by a process for preparing ENB according to the present invention which comprises isomerizing VNB in the presence of at least one catalyst selected from a group consisting of a solid base catalyst which is prepared by reacting alumina and an alkali metal hydroxide in a temperature range of 200° to 500° C. and then reacting the reaction product with an alkali metal in a temperature range of 180° to 350° C. and a solid base catalyst which is prepared by reacting water-containing alumina and an alkali metal in such an amount that corresponds to a molar equivalent of water contained in alumina at a temperature in a range between a melting point of the alkali metal and 500° C. and then reacting the reaction product with an alkali metal in a temperature range of 180° to 350° C.

DETAILED DESCRIPTION OF THE INVENTION

The process of the present invention has been completed based on the finding that, in isomerization of VNB to ENB, catalytic performance of the catalyst is influenced by preparation temperatures, namely, (1) a temperature at which alumina, the alkali metal hydroxide and the alkali metal are reacted, particularly, the alkali metal is reacted in the preparation, and (2) a temperature at which water-containing alumina and the alkali metal are reacted, particularly, water-containing alumina is reacted with the excess portion of the alkali metal to the molar amount of water contained in alumina.

Examples of the alkali metal hydroxide are lithium hydroxide, sodium hydroxide, potassium hydroxide, rubidium hydroxide cesium hydroxide and mixtures thereof. The alkali metal hydroxide may be used in a solid or liquid state.

As the alkali metal, an alkali metal of Group I of the Periodic Table such as sodium, potassium and rubidium is used. They may be used as a mixture or an alloy. Among them, sodium, potassium and an alloy of them are preferred.

As a combination of the alkali metal and the alkali metal hydroxide, a combination of an alkali metal and a hydroxide of other alkali metal, for example a combination of potassium and sodium hydroxide, of sodium and potassium hydroxide or of sodium and lithium hydroxide can be used, although a combination of an alkali metal and its corresponding hydroxide, for example, a combination of sodium and sodium hydroxide, of potassium and potassium hydroxide, and the like may be used. A combination of metal sodium and sodium hydroxide is practically preferred. Amounts of the alkali metal and the alkali metal hydroxide are 2 to 10% by weight and 5 to 40 % by weight, respectively based on the weigh of alumina in view of the catalytic activity.

Usually, alumina with a relatively large surface area such as γ-, χ-, β- and η-alumina is used. Among them, alumina of 50 to 500 mesh, particularly, γ-alumina of such mesh is preferred in view of the catalytic activity. Since alumina also acts as a carrier it reacts with the alkali metal and the alkali metal hydroxide. An alumina-containing compound such as kaolin and alumina silicate may be used in place of alumina but is less preferable.

According to the present invention, alumina, the alkali metal and the alkali metal hydroxide are reacted at a specific temperature as described above to prepare the solid base catalyst. As to the sequence of the reactions, preferably, alumina and the alkali metal hydroxide are firstly reacted and then the alkali metal is reacted. Usually, the alkali metal hydroxide kept at a temperature higher than its melting point is added to alumina and reacted at the specific temperature, although an aqueous solution of the alkali metal hydroxide may be used and the reaction mixture is heated to the specific temperature to proceed the reaction. Also, the alkali metal is added at a temperature higher than its melting point and reacted at the specific temperature, although it can be added in the form of a solution and heated to the specific temperature to proceed the reaction. The reactions are preferably carried out in an atmosphere of an inert gas such as nitrogen, helium and argon.

In the present invention, the properties of the prepared solid base catalyst are influenced by the reaction temperatures. Particularly, the catalytic activity of the catalyst is greatly affected by the temperature at which the alkali metal is reacted.

Alumina and the alkali metal hydroxide are reacted in a temperature range of 200° to 500° C., preferably 250° to 450° C., and the alkali metal is reacted in a temperature range of 180° to 350° C., preferably 200° to 330° C.

By reacting the compounds at such temperatures, the catalyst with significantly high activity is prepared. Therefore, the isomerization of VNB to ENB can be efficiently achieved even with a small amount of the catalyst.

The reaction time varies with other reaction conditions such as temperature. The reaction of alumina and the alkali metal hydroxide may be completed within 0.5 to 10 hours, and that of the alkali metal may be completed within 10 to 300 minutes.

In addition to the above method, the solid base catalyst to be used in the process of the present invention can be prepared by reacting water-containing alumina and the alkali metal. This may be due to the formation of the alkali metal hydroxide from water contained in alumina and the alkali metal. Such preparation of the catalyst will be illustrated hereinafter.

Various types of water-containing alumina except $\alpha$-alumina can be used.

Generally, alumina is produced by calcining aluminum hydroxide. According to the calcining temperature and time, alumina has various metastable states and the water content varies so that various kinds of alumina are produced. In the present invention, such alumina may be used. Preferably, water-containing alumina with a large surface area such as $\gamma$-, $\chi$-, $\rho$- and $\eta$-alumina is used.

Although it is rather difficult to measure water content of alumina, water content may be expressed by weight loss on heating in the heating step in which alumina in its original state is changed to $\alpha$-alumina which is considered to include no removable water. Usually, the water content of water-containing alumina is 1.3 to 10% by weight, preferably 2 to 7% by weight in terms of weight loss on heating.

The alkali metal used in this preparation is the same as described above. The total amount of the alkali metal to be reacted is larger than such amount that corresponds to a molar equivalent of water contained in alumina, preferably 1.01 to 2 time molar equivalents of water contained in alumina.

According to the present invention, water-containing alumina is reacted with the alkali metal in at least such an amount that corresponds to the molar equivalent of water contained in alumina preferably in an atmosphere of an inert gas such as nitrogen, helium and argon, and then excess amount alkali metal is reacted with alumina. In this method, the alkali metal firstly reacted and that of the alkali metal subsequently reacted may be the same or different.

Also in this second preparation of the solid base catalyst, the reaction temperatures, particularly, the reaction temperatures in the second step have significant influences on the properties of the catalyst.

In the first reaction of water-containing alumina and the alkali metal in an amount corresponding to the molar equivalent of contained water, a reaction temperature is in a range between a melting point of the alkali metal and 500° C. In the second reaction of alumina and excess alkali metal, a reaction temperature is 180° to 350° C., preferably 200° to 330° C. Preferably, the first reaction temperature and the second reaction temperature are substantially the same. In such case, the reaction temperature is preferably from 180° to 350° C., more preferably from 200° to 330° C. In this case, the alkali metal can be added in one portion.

By reacting the compounds at such temperatures, the catalyst with significantly high activity is prepared. Therefore, the isomerization of VNB to ENB can be efficiently achieved even with a small amount of the catalyst.

The reaction time varies with other reaction conditions such as the reaction temperature. Usually, it is 15 minutes to 10 hours.

Thus, the solid base catalysts with greatly increased activity in comparison with the conventional catalysts are prepared.

In the process of the invention, VNB is isomerized to ENB in the presence of the solid base catalyst as prepared above. A weight ratio of the catalyst to VNB is 1:3,000 to 1:50, preferably 1:2,000 to 1:100. Since the isomerization proceeds at an ordinary temperature, it is not necessary to heat the reaction system. To accelerate the isomerization, the reaction temperature may be elevated. Usually, the reaction temperature is in a range between −30° to +120° C., preferably between −10° to +100° C.

The isomerization is carried without any reaction medium, although it may be carried out in an inert liquid medium such as a hydrocarbon (e.g., hexane, heptane and dodecane).

The isomerization of the present invention may be carried out batch wise or continuously. The isomerization is preferably carried at an atmosphere of an inert gas. If necessary, VNB is pretreated with a desiccant such as alumina prior to isomerization.

The isomerization product is analyzed by a known method such as gas chromatography and separated from the catalyst by a conventional separation method such as filtration.

According to the present invention, ENB can be prepared by isomerization of VNB in a high yield substantially without formation of by-products such as a polymer in the presence of the catalyst in a much smaller amount than the conventional catalyst. Further, the isomerization can be safely carried out without any fear of ignition.

Practically and presently preferred embodiments of the present invention will be illustrated by following examples.

REFERENCE EXAMPLE 1

To a 100 ml flask, $\gamma$-alumina (31.9 g) was added and heated to 490°–500° C. under nitrogen with stirring at the same temperature for one hour. After cooling to 300°–310° C., sodium hydroxide (4.5 g) was added thereto and stirred at the same temperature for 3 hours.

Then, metal sodium (1.5 g) was added, stirred at the same temperature for one hour and then cooled to room temperature to obtain a solid base (34.9 g).

EXAMPLE 1

TABLE 1

| Reference Example No. | γ-Alumina (g) | Addition conditions of alkali metal hydroxide | | | | Addition conditions of alkali metal | | | | Yield of solid base (g) |
|---|---|---|---|---|---|---|---|---|---|---|
| | | MOH | Amount (g) | Temp. (°C.) | Stirring time (hr) | Alkali metal | Amount (g) | Temp. (°C.) | Stirring time (hr) | |
| 3 | 31.9 | NaOH | 3.0 | 390–400 | 1 | Na | 1.35 | 290–300 | 1 | 33.7 |
| 4 | 31.9 | KOH | 3.0 | 340–350 | 3 | K | 1.5 | 200–210 | 1 | 33.2 |
| 5 | 31.9 | NaOH | 3.0 | 310–320 | 3 | K | 1.5 | 240–250 | 1 | 33.7 |
| 6 | 31.9 | NaOH | 3.0 | 310–320 | 3 | Na | 1.5 | 230–240 | 3 | 33.7 |
| 7 | 32.0 | NaOH | 3.0 | 300–310 | 3 | Na | 2.1 | 300–310 | 1 | 33.7 |
| 8 | 31.9 | NaOH | 3.0 | 335–345 | 3 | Na | 1.5 | 335–345 | 1 | 33.6 |
| 9 | 31.9 | NaOH | 3.0 | 300–310 | 3 | Na:K alloy (atomic ratio = 1:1) | 1.5 | 180–190 | 1 | 33.7 |
| 10 | 31.9 | NaOH | 3.0 | 390–400 | 3 | Na | 1.5 | 390–400 | 1 | 33.8 |
| 11 | 31.9 | NaOH | 3.0 | 300–310 | 3 | Na | 1.5 | 150–160 | 2 | 33.5 |

TABLE 2

| Example No. | Solid base catalyst | | Amount of VNB (g) | Reaction conditions | | Reaction results | | |
|---|---|---|---|---|---|---|---|---|
| | Ref. Ex. No. | Amount (g) | | Temp. (°C.) | Time (hrs) | Yield (g) | VNB (%) | ENB (%) |
| 2 | 2 | 0.24 | 120 | 15–20 | 6 | 119.7 | 0.6 | 99.8 |
| 3 | 3 | 0.25 | 68.5 | 15–20 | 6 | 68.1 | 0.3 | 99.6 |
| 4 | 4 | 0.25 | 65.5 | 15–20 | 6 | 65.0 | 0.3 | 99.5 |
| 5 | 5 | 0.24 | 61.4 | 15–20 | 6 | 60.9 | 0.3 | 99.2 |
| 6 | 6 | 0.26 | 67.6 | 15–20 | 8 | 67.0 | 1.1 | 98.8 |
| 7 | 7 | 0.24 | 62.6 | 15–20 | 6 | 62.1 | 0.6 | 99.3 |
| 8 | 8 | 0.27 | 54.1 | 15–20 | 6 | 53.7 | 0.3 | 99.6 |
| 9 | 9 | 0.25 | 49.0 | 15–20 | 7 | 48.4 | 0.4 | 99.5 |
| Comp. 1 | 10 | 0.25 | 39.3 | 15–20 | 8 | 38.8 | 26.0 | 73.9 |
| Comp. 2 | 11 | 0.25 | 41.8 | 15–20 | 8 | 41.4 | 93.3 | 6.6 |

To a 200 ml flask, VNB (82.5 g) was added under nitrogen. The solid base prepared in Reference Example 1 (0.25 g) was added and stirred at a temperature of 15° to 20° C. for 6 hours.

The solid catalyst was filtered off to obtain a reaction mixture (81.9 g). Gas chromatographic analysis of the mixture revealed that 99.4% of ENB and 0.5% of VNB were contained in the mixture.

REFERENCE EXAMPLE 2

To a 100 ml flask, γ-alumina (31.9 g) was added and heated to 490°–500° C. under nitrogen with stirring at the same temperature for one hour. After cooling to 300°–310° C., sodium hydroxide (3.0 g) was added thereto and stirred at the same temperature for 3 hours. Thereafter, metal sodium (1.2 g) and metal potassium (0.3 g) were added, stirred at the same temperature for 30 minutes and then cooled to room temperature to obtain a solid base (33.8 g).

REFERENCE EXAMPLES 3–11

In the same manner as in Reference Example 1 but carrying out the reaction under the conditions specified in Table 1, a solid base catalyst was prepared.

EXAMPLES 2–9 and COMPARATIVE EXAMPLES 1–2

In the same manner as in Example 1 but using the solid base catalyst prepared in each of Reference Examples 2–9 and Comparative Examples 1–2, VNB was isomerized. The results are shown in Table 2.

REFERENCE EXAMPLE 12

To a 100 ml flask, γ-alumina containing 2.2% by weight of water (30.0 g) was added and heated to 300° C. in a nitrogen stream with stirring at the same temperature for one hour. Metal sodium (1.2 g) was added thereto, stirred at the same temperature for one hour and then cooled to room temperature to obtain a grayish blue solid base (30.9 g).

EXAMPLE 10

To a 200 ml flask in a nitrogen atmosphere, the solid base catalyst prepared in Reference Example 12 (0.25 g) and then VNB (64.5 g) were added and stirred at a temperature of 15°–20° C. for 8 hours. Thereafter, the catalyst was filtered off to obtain a reaction mixture (63.9 g). Gas chromatographic analysis of the mixture revealed that 99.5% of ENB and 0.4% of VNB were contained in the mixture.

REFERENCE EXAMPLES 13–21

In the same manner as in Reference Example 12 but carrying out the reaction under the conditions specified in Table 3, a solid base was prepared.

EXAMPLES 11–15 and COMPARATIVE EXAMPLES 3–6

In the same manner as in Example 10 but using, as a catalyst, the solid base prepared in each of Reference Examples 13–21 and Comparative Examples 3–6, VNB was isomerized. The results are shown in Table 4.

TABLE 3

| Reference Example No. | γ-Alumina Water content (wt %) | Amount (g) | Conditions for reacting alkali metal Alkali metal | Amount (g) | Temp. (°C.) | Stirring time (hr) | Solid base catalyst Color | Yield (g) |
| --- | --- | --- | --- | --- | --- | --- | --- | --- |
| 13 | 2.2 | 30.0 | Na:K alloy (Atomic ratio = 1:1) | 1.2 | 200 | 1 | Grayish blue | 31.0 |
| 14 | 2.2 | 30.0 | Na | 1.2 | 350 | 1 | Grayish blue | 30.7 |
| 15 | 3.8 | 30.0 | Na | 2.1 | 310 | 1 | Gray | 31.8 |
| 16 | 2.2 | 30.0 | K | 1.5 | 200 | 1 | Grayish blue | 31.2 |
| 17 | 1.6 | 30.0 | Na | 0.98 | 300 | 1 | Gray | 30.8 |
| 18 | 2.2 | 30.0 | Na | 1.2 | 150 | 1 | Dark gray | 31.2 |
| 19 | 2.2 | 30.0 | Na | 1.2 | 400 | 1 | Grayish blue | 30.9 |
| 20 | 2.2 | 30.0 | Na | 1.8 | 300 | 1 | Dark gray | 31.7 |
| 21 | 1.4 | 30.0 | Na | 1.35 | 300 | 1 | Dark gray | 31.3 |

TABLE 4

| Example No. | Solid base catalyst Ref. Ex. No. | Amount (g) | Amount of VNB (g) | Reaction conditions Temp. (°C.) | Time (hrs) | Reaction results Yield (g) | VNB (%) | ENB (%) |
| --- | --- | --- | --- | --- | --- | --- | --- | --- |
| 11 | 13 | 0.24 | 65.3 | 15–20 | 8 | 64.8 | 0.3 | 99.6 |
| 12 | 14 | 0.25 | 50.0 | 15–20 | 8 | 49.7 | 0.5 | 99.4 |
| 13 | 15 | 0.26 | 72.0 | 15–20 | 8 | 71.5 | 0.5 | 99.4 |
| 14 | 16 | 0.24 | 62.4 | 15–20 | 8 | 61.9 | 0.3 | 99.6 |
| 15 | 17 | 0.22 | 47.3 | 15–20 | 8 | 46.9 | 0.5 | 99.4 |
| Comp. 3 | 18 | 0.24 | 41.5 | 15–20 | 24 | 41.0 | 94.1 | 5.9 |
| Comp. 4 | 19 | 0.25 | 39.5 | 15–20 | 16 | 38.9 | 57.5 | 42.4 |
| Comp. 5 | 20 | 0.24 | 50.2 | 15–20 | 16 | 49.7 | 65.4 | 35.6 |
| Comp. 6 | 21 | 0.24 | 36.7 | 15–20 | 16 | 36.2 | 57.4 | 42.5 |

REFERENCE EXAMPLE 22

To a 100 ml flask, alumina comprising γ-alumina and containing 6.0% by weight of water (50 g) was added and heated to 200° C. with stirring and injecting nitrogen. At the same temperature, metal sodium (4.0 g) was added by portions over 20 minutes. After stirring for one hour, it was gradually heated to 300° C. At said temperature, additional metal sodium (1.9 g) was added by portions over 10 minutes and stirred at the same temperature for 3.5 hours to obtain a solid base (54.2 g).

REFERENCE EXAMPLE 23

To a 100 ml flask, alumina comprising γ-alumina and containing 6.0% by weight of water (50 g) was added and heated to 200° C. with stirring under nitrogen. At the same temperature, metal sodium (4.0 g) was added by portions over 20 minutes. After stirring for one hour, it was gradually heated to 400° C. At said temperature, additional metal sodium (1.9 g) was added by portions over 10 minutes and stirred at the same temperature for 3.5 hours to obtain a solid base (54.1 g).

EXAMPLE 16

To a 200 ml flask in a nitrogen atmosphere, the solid base prepared in Reference Example 22 (0.25 g) and then VNB (62.5 g) were added and stirred at 15°–20° C. for 8 hours.

The solid catalyst was filtered off to obtain a reaction mixture (62.0 g). Gas chromatographic analysis of the mixture revealed that 99.5% of ENB and 0.3% of VNB were contained in the mixture.

COMPARATIVE EXAMPLE 7

To a 200 ml flask in a nitrogen atmosphere, the solid base prepared in Reference Example 23 (0.25 g) and then VNB (62.5 g) were added and stirred at 15°–20° C. for 8 hours.

The solid catalyst was filtered off to obtain a reaction mixture (61.9 g). Gas chromatographic analysis of the mixture revealed that 59.8% of ENB and 40.1% of VNB were contained in the mixture.

What is claimed is:

1. A process for preparing 5-ethylidene-2-norbornene which comprises isomerizing 5-vinyl-2-norbornene in the presence of at least one catalyst selected from a group consisting of (a) a solid base catalyst which is prepared by reacting alumina and a alkali metal hydroxide at a temperature of 200° to 500° C. and then reacting the reaction product with an alkali metal at a temperature of 180° to 350° C. and (b) a solid base catalyst which is prepared by reacting water-containing alumina and an alkali metal in such an amount that corresponds to a molar equivalent of water contained in the alumina at a temperature in a range between a melting point of the alkali metal and 500° C. and then reacting the reaction product with the alkali metal in such an amount that the total amount of alkali metal corresponds to 1.01 to 2 times molar equivalent of water contained in alumina, at a temperature of 180° to 350° C.

2. The process according to claim 1, wherein the solid base catalyst is prepared by heating alumina, an alkali metal hydroxide and an alkali metal.

3. The process according to claim 2, wherein alumina and the alkali metal hydroxide are reacted in a temperature range of 250° to 450° C.

4. The process according to claim 2, wherein the alkali metal is reacted in a temperature range of 200° to 330° C.

5. The process according to claim 2, wherein the alkali metal hydroxide is selected from the group consisting of lithium hydroxide, sodium hydroxide, potassium hydroxide, cesium hydroxide and mixtures thereof.

6. The process according to claim 2, wherein alumina is selected from the group consisting of γ-alumina, χ-alumina, ρ-alumina, η-alumina and mixtures thereof.

7. The process according to claim 1, wherein the solid base catalyst is prepared by heating water-containing alumina and an alkali metal.

8. The process according to claim 7, wherein the water-containing alumina and the excess portion of the alkali metal to the molar equivalent of water contained in alumina are reacted at a temperature of 200° to 330° C. in the preparation of the catalyst.

9. The process according to claim 7, wherein alumina and the molar equivalent amount of the alkali metal, and alumina and the excess molar equivalent amount of the alkali metal are reacted at a temperature of 200° to 330° C. in the preparation of the catalyst.

10. The process according to claim 7, wherein water-containing alumina is selected from the group consisting of γ-alumina, χ-alumina and ρ-alumina which are preferably prepared by calcination of aluminum hydroxide.

11. The process according to claim 7, wherein the water content of alumina is 1.3 to 10% by weight.

12. The process according to claim 7, wherein the water content of alumina is 2 to 7% by weight.

13. The process according to claim 7, wherein the alkali metal is at least one selected from the group consisting of sodium, potassium and rubidium and mixtures and alloys thereof.

14. The process according to claim 1, wherein a weight ratio of the solid base catalyst to 5-vinyl-2-norbornene is from 1:2,000 to 1:100.

15. The process according to claim 1, wherein the isomerization temperature range is from −10° to +100° C.

16. A process for preparing 5-etylidene-2-norbornene which comprises isomerizing 5-vinyl-2-norbornene in the presence of a solid base catalyst which is prepared by reacting water-containing alumina and an alkali metal in such an amount that corresponds to a molar equivalent of water contained in the alumina at a temperature in a range between a melting point of the alkali metal and 500° C. and then reacting the reaction product with the alkali metal in such an amount that the total amount of alkali metal corresponds to 1.01 to 2 times molar equivalent of water contained in alumina at a temperature of 180° to 350° C.

* * * * *